(12) United States Patent
Lampropoulos et al.

(10) Patent No.: US 10,842,973 B2
(45) Date of Patent: *Nov. 24, 2020

(54) MECHANICALLY ASSISTED INFLATION DEVICE HANDLE AND METHOD OF USE

(71) Applicant: Merit Medical Systems, Inc., South Jordan, UT (US)

(72) Inventors: Fred Lampropoulos, Salt Lake City, UT (US); Brian Stevens, Pleasant Grove, UT (US); William Padilla, Sandy, UT (US); Gregory R. McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,680

(22) Filed: Jun. 6, 2016

(65) Prior Publication Data

US 2016/0279395 A1 Sep. 29, 2016

Related U.S. Application Data

(63) Continuation of application No. 13/970,292, filed on Aug. 19, 2013, now Pat. No. 9,987,471, which is a continuation of application No. 13/464,046, filed on May 4, 2012, now Pat. No. 8,545,442.

(60) Provisional application No. 61/483,564, filed on May 6, 2011.

(51) Int. Cl.
*A61M 25/10* (2013.01)

(52) U.S. Cl.
CPC .. *A61M 25/1018* (2013.01); *A61M 25/10181* (2013.11); *A61M 25/10182* (2013.11); *A61M 25/10184* (2013.11); *A61M 25/10* (2013.01)

(58) Field of Classification Search
CPC ........ A61M 25/1018; A61M 25/10181; A61M 25/10182

See application file for complete search history.

(56) References Cited

U.S. PATENT DOCUMENTS

| 3,495,494 | A | | 2/1970 | Scott |
| 4,919,121 | A | | 4/1990 | Rydell et al. |
| 5,011,476 | A | | 4/1991 | Foster |
| 5,047,015 | A | * | 9/1991 | Foote .............. A61M 25/10182 604/99.01 |

(Continued)

FOREIGN PATENT DOCUMENTS

| CA | 2049067 | 9/1998 |
| EP | 0565045 A1 | 10/1993 |

(Continued)

OTHER PUBLICATIONS

Office Action dated Aug. 8, 2017 for U.S. Appl. No. 13/970,292.

(Continued)

*Primary Examiner* — Jenna Zhang
(74) *Attorney, Agent, or Firm* — Stoel Rives LLP

(57) ABSTRACT

An inflation device including a handle mechanism configured to selectively engage and disengage threads within the device. In some instances the threads are configured to couple a plunger to a syringe body. The handle mechanism may be configured to (1) provide a mechanical advantage and (2) change the location and direction of the input force, thereby making the device easier to use.

20 Claims, 8 Drawing Sheets

(56) References Cited

U.S. PATENT DOCUMENTS

| | | | |
|---|---|---|---|
| 5,057,078 A * | 10/1991 | Foote | A61M 5/315 |
| | | | 604/224 |
| 5,163,904 A | 11/1992 | Lampropoulos et al. | |
| 5,168,757 A | 12/1992 | Rabenau et al. | |
| 5,209,732 A * | 5/1993 | Lampropoulos | A61M 25/104 |
| | | | 604/99.01 |
| 5,279,563 A | 1/1994 | Brucker et al. | |
| 5,306,248 A | 4/1994 | Barrington | |
| 5,336,183 A | 8/1994 | Greelis et al. | |
| 5,425,713 A | 1/1995 | Taylor et al. | |
| 5,453,091 A | 9/1995 | Taylor et al. | |
| 5,507,727 A * | 4/1996 | Crainich | A61M 25/1018 |
| | | | 604/97.02 |
| 5,554,132 A | 9/1996 | Straits et al. | |
| 5,571,133 A | 11/1996 | Yoon | |
| D376,357 S | 12/1996 | Ferland | |
| 5,609,604 A | 3/1997 | Schwemberger | |
| 5,674,237 A | 10/1997 | Ott | |
| 5,713,242 A | 2/1998 | Kanner et al. | |
| D401,324 S | 11/1998 | Hjertman et al. | |
| 5,921,968 A * | 7/1999 | Lampropoulos | A61M 39/0613 |
| | | | 604/167.05 |
| 6,050,972 A | 4/2000 | Zadno-Azizi et al. | |
| 6,106,496 A | 8/2000 | Arnissolle | |
| D489,456 S | 5/2004 | Groenke et al. | |
| 6,796,959 B2 | 9/2004 | Davis et al. | |
| 6,936,034 B2 | 8/2005 | Watkins | |
| D545,429 S | 6/2007 | Hayes | |
| D547,841 S | 7/2007 | Ziemann | |
| 7,291,132 B2 | 11/2007 | DeRuntz et al. | |
| 7,351,223 B2 | 4/2008 | Call | |
| 7,530,970 B2 | 5/2009 | McArthur et al. | |
| 7,892,202 B2 | 2/2011 | Lampropoulos et al. | |
| 8,118,776 B2 | 2/2012 | Lampropoulos et al. | |
| 8,137,307 B2 | 3/2012 | Tennican et al. | |
| D661,389 S | 6/2012 | Morgan et al. | |
| D667,950 S | 9/2012 | Hyun et al. | |
| D683,452 S | 5/2013 | Davies | |
| 8,506,572 B2 | 8/2013 | Evans et al. | |
| D690,417 S | 9/2013 | Solomon | |
| 8,545,442 B2 | 10/2013 | Lampropoulos et al. | |
| D710,496 S | 8/2014 | Stevens et al. | |
| D726,311 S | 4/2015 | Lampropoulos et al. | |
| D731,054 S | 6/2015 | Lampropoulos et al. | |
| 2009/0099517 A1 | 4/2009 | Steadham | |
| 2010/0010470 A1 | 4/2010 | McCabe | |
| 2010/0116360 A1 | 5/2010 | Kanner et al. | |
| 2010/0168677 A1 | 7/2010 | Gabriel et al. | |
| 2011/0046604 A1 | 2/2011 | Felsovalyi et al. | |
| 2013/0116655 A1 | 5/2013 | Bacino et al. | |
| 2013/0123693 A1 | 5/2013 | Lampropoulos et al. | |
| 2014/0263403 A1 | 9/2014 | Conner et al. | |
| 2015/0051543 A1 | 2/2015 | Chadwick et al. | |

FOREIGN PATENT DOCUMENTS

| | | |
|---|---|---|
| JP | 04504072 | 7/1992 |
| JP | 2001523535 | 3/2003 |
| KP | 1020110025578 | 10/2011 |
| KP | 1020130047657 | 8/2013 |
| WO | 199011101 | 10/1990 |
| WO | 1999026692 | 6/1997 |
| WO | 199744077 | 11/1997 |
| WO | 2012154539 | 11/2012 |
| WO | 2015023923 A1 | 2/2015 |

OTHER PUBLICATIONS

Office Action dated Sep. 5, 2017 for U.S. Appl. No. 14/460,650.
European Search Report dated Mar. 7, 2017 for EP14836509.1.
European Search Report dated Sep. 15, 2016 for EP12782669.1.
Office Action dated Feb. 15, 2017 for U.S. Appl. No. 13/970,292.
Extended European Search Report dated Jul. 15, 2015 for EP12782669.1.
International Search Report and Written Opinion dated Aug. 17, 2012 for PCT/US2012/036473.
International Search Report and Written Opinion dated Nov. 19, 2014 for PCT/US2014/051219.
Notice of Allowance dated Jan. 12, 2015 for U.S. Appl. No. 29/424,608.
Notice of Allowance dated Mar. 4, 2015 for U.S. Appl. No. 29/424,608.
Notice of Allowance dated Mar. 13, 2015 for U.S. Appl. No. 29/430,061.
Notice of Allowance dated Apr. 4, 2014 for U.S. Appl. No. 29/405,006.
Notice of Allowance dated Aug. 7, 2013 for U.S. Appl. No. 13/464,046.
Office Action dated Jan. 2, 2015 for U.S. Appl. No. 29/430,061.
Office Action dated Apr. 12, 2013 for U.S. Appl. No. 13/464,046.
Office Action dated Jul. 11, 2016 for U.S. Appl. No. 13/970,292.
Office Action dated Aug. 28, 2014 for U.S. Appl. No. 29/424,608.
Office Action dated Dec. 20, 2013 for U.S. Appl. No. 29/405,006.
Notice of Allowance dated Mar. 30, 2018 for U.S. Appl. No. 13/970,272.
Office Action dated Feb. 14, 2019 for U.S. Appl. No. 29/578,120.
Office Action dated Jan. 15, 2019 for U.S. Appl. No. 14/460,650.
European Examination Report dated Mar. 28, 2019 for EP14836509.1.
Office Action dated Jul. 8, 2019 for U.S. Appl. No. 14/460,650.
Notice of Allowance dated Nov. 6, 2019 for U.S. Appl. No. 29/578,120.
Office Action dated Mar. 10, 2020 for U.S. Appl. No. 14/460,650.

* cited by examiner

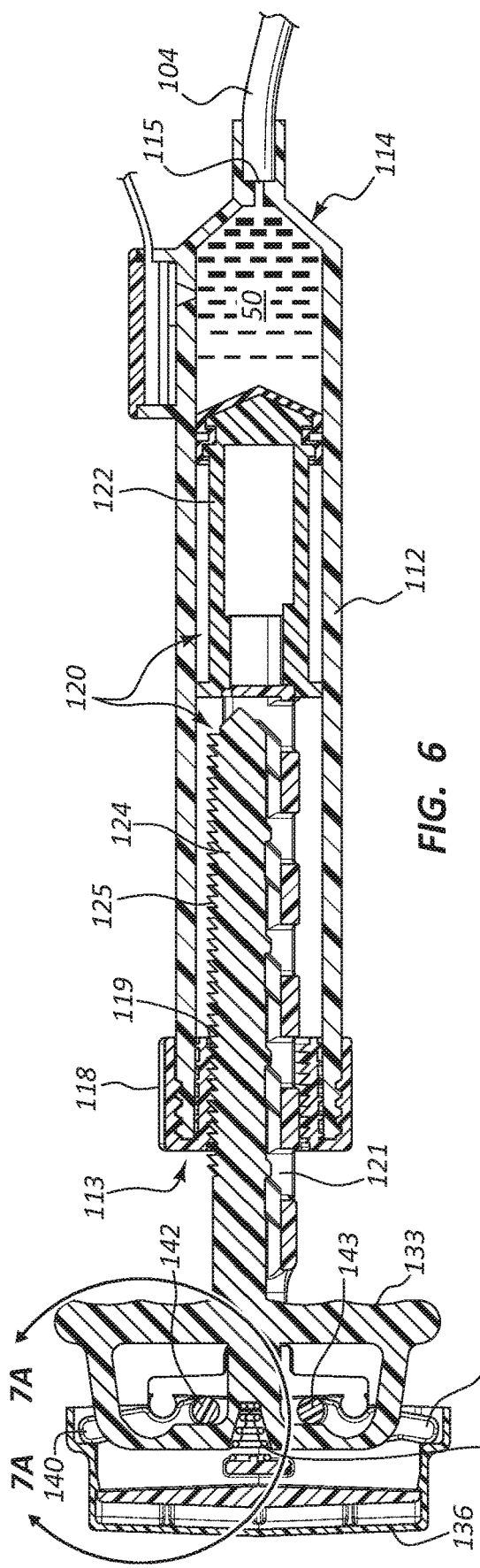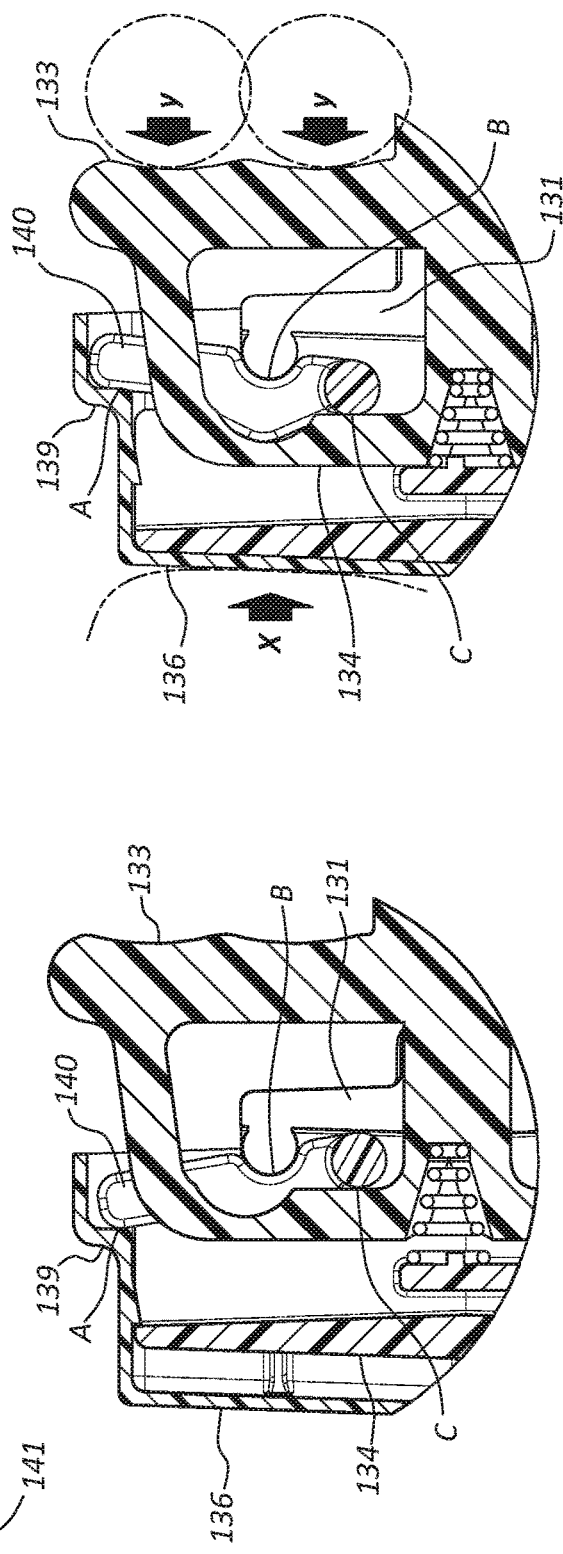
FIG. 6
FIG. 7A
FIG. 7B

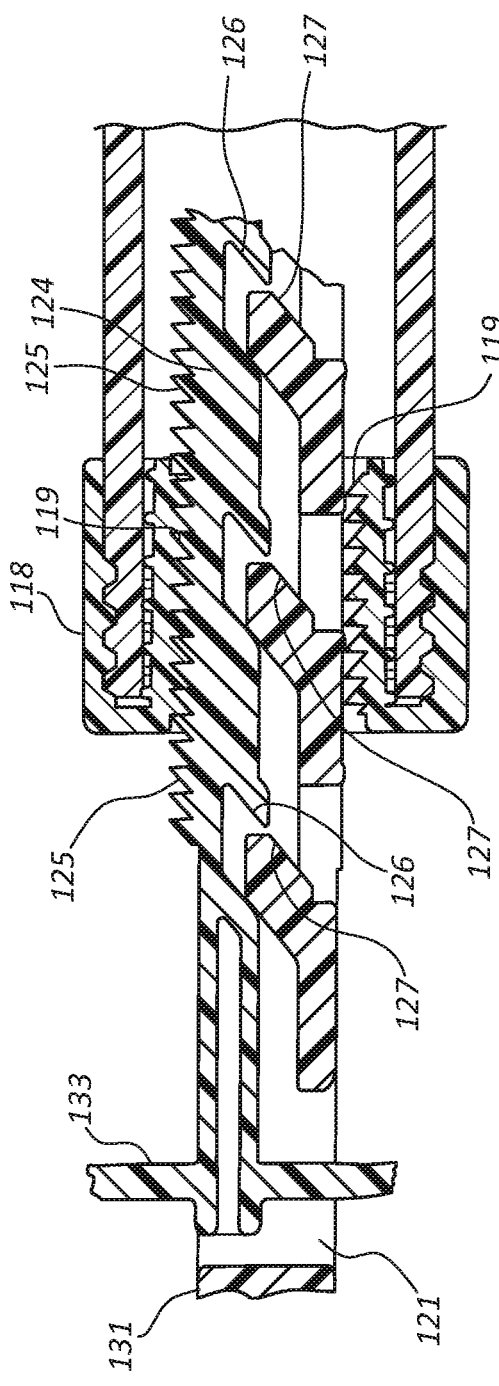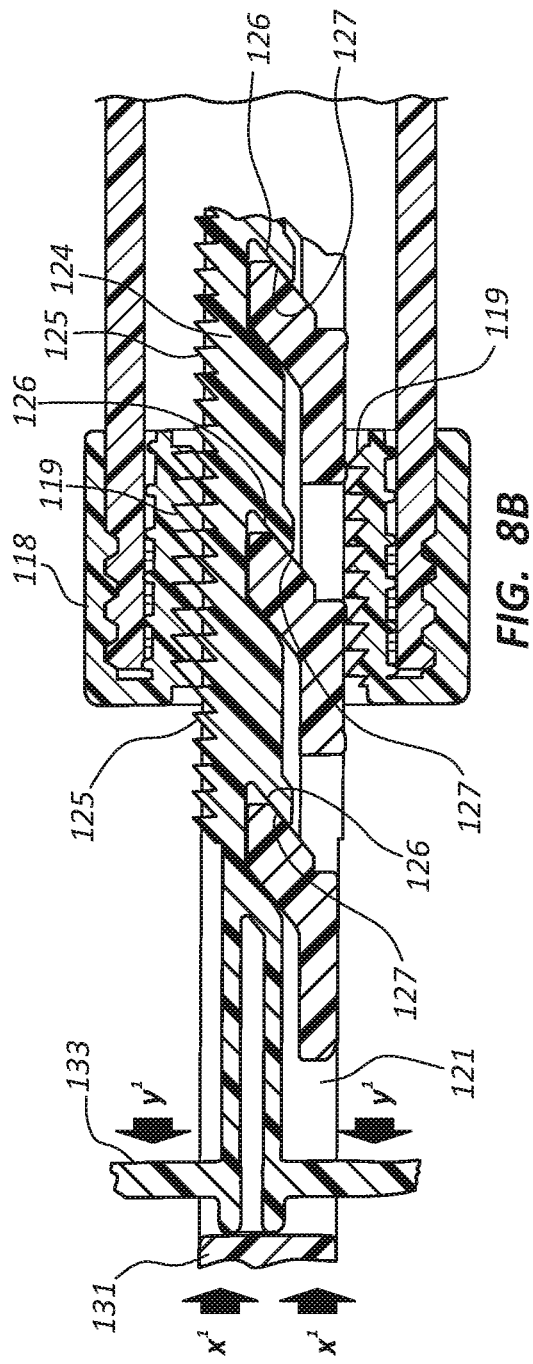

US 10,842,973 B2

MECHANICALLY ASSISTED INFLATION DEVICE HANDLE AND METHOD OF USE

RELATED APPLICATIONS

The present application is a continuation of U.S. patent application Ser. No. 13/970,292, titled "Mechanically Assisted Inflation Device Handle and Method of Use," filed on Aug. 19, 2013, which is a continuation of U.S. patent application Ser. No. 13/464,046, titled "Mechanically Assisted Inflation Device Handle and Method of Use," filed May 4, 2012, now issued as U.S. Pat. No. 8,545,422, which in turn claims priority to U.S. Provisional Application No. 61/483,564, titled "Mechanically Assisted Inflation Device Handle and Method of Use," filed on May 6, 2011, the contents of each of which are herein incorporated by reference in their entirety.

TECHNICAL FIELD

The present disclosure relates generally to devices used to pressurize, depressurize, or otherwise displace fluid, particularly in medical devices. More specifically, the present disclosure relates to devices used to pressurize, depressurize, or otherwise displace fluid along a line in order to inflate or deflate a medical device, such as a balloon.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 6 is a cross sectional view of the inflation device of FIG. 1 with fluid disposed in a portion of the device.

FIG. 7A is a close up view, taken through line 7A-7A, of a portion of the handle of FIG. 6 in a first position.

FIG. 7B is the portion of the handle of FIG. 7A in a second position.

FIG. 8A is a cross sectional view of the threaded portion of the inflation device of FIG. 1 in a first position.

FIG. 8B is the cross sectional view of the threaded portion of the inflation device of 8A in a second position.

DETAILED DESCRIPTION

Figure 1:
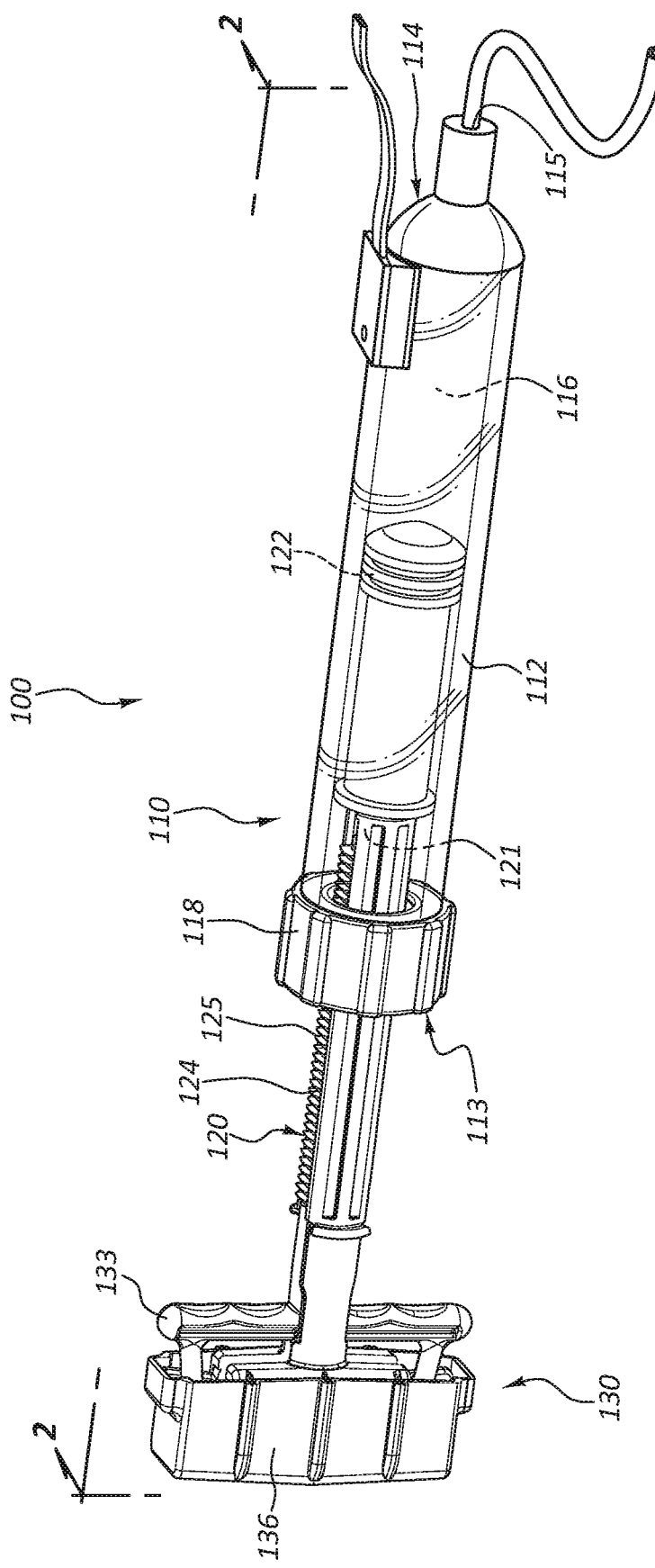
FIG. 1 is a perspective view of an inflation device.

An inflation device may include a syringe which utilizes threads to advance or retract a plunger by rotating the plunger handle relative to the body of the syringe such that the threads cause longitudinal displacement of the plunger relative to the body. In some instances, an inflation syringe may further include retractable threads, enabling a practitioner to disengage the threads and displace the plunger simply pushing or pulling the plunger.

Certain inflation devices, such as those described in U.S. Pat. Nos. 5,047,015; 5,057,078; 5,163,904; and 5,209,732 include a mechanism in the handle of the device which allows the practitioner to disengage the threads through manipulating the mechanism. For example, in some instances the handle of such a device may include a "trigger" portion which may be configured to retract threads positioned on the plunger when the trigger is actuated.

An inflation device may further be configured such that the thread retraction mechanism includes elements which provide mechanical advantage, allowing a user to more easily manipulate the mechanism. Moreover, a mechanism may be configured to alter the location of an input force, which may provide flexibility and ease of operation to the device.

It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

"Fluid" is used in its broadest sense, to refer to any fluid, including both liquids and gasses as well as solutions, compounds, suspensions, etc., which generally behave as a fluid.

FIGS. 1-9 illustrate different views of an inflation device. In certain views the device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure.

FIG. 1 is a perspective view of an inflation device 100. In the illustrated embodiment, the inflation device 100 is partially comprised of a syringe 110. The inflation device 100 includes three broad groups of components; each group may have numerous subcomponents and parts. The three broad component groups are: a body component such as syringe body 112, a pressurization component such as plunger 120, and a handle 130.

The syringe body 112 may be formed of a generally cylindrical hollow tube configured to receive the plunger 120. The syringe body 112 may include an inlet/outlet port 115 located adjacent the distal end 114 of the syringe body 112. In some embodiments, a nut 118 may be coupled to the syringe body 112 adjacent the proximal end 113 of the syringe body 112. The nut 118 may include a center hole configured to allow the plunger 120 to pass through the nut 118 into the syringe body 112. Further, the nut 118 may include internal nut threads 119 (FIG. 2) configured to selectively couple the nut 118 to the plunger 120 in some embodiments.

The plunger 120 may be configured to be longitudinally displaceable within the syringe body 112. The plunger 120 may be comprised of a plunger shaft 121 coupled to a plunger seal 122 at the distal end of the plunger shaft 121. The plunger shaft 121 may also be coupled to the handle 130 at the proximal end of the plunger shaft 121, the plunger shaft 121 spanning the distance between the plunger seal 122 and the handle 130.

The handle 130 broadly refers to the group of components coupled to the proximal end of the plunger 120, some of which may be configured to be graspable by a user. In certain embodiments the handle 130 may be configured such that the user may manipulate the position of the plunger 112 by manipulating the handle 130. Further, in some embodiments the handle 130 may be an actuator mechanism, configured to manipulate components of the inflation device 100.

Any and every component disclosed in connection with any of the exemplary handle configurations herein may be optional. That is, though the handle 130 broadly refers to the components coupled to the proximal end of the plunger shaft 121 which may be configured to be graspable by a user, use of the term "handle" is not meant to indicate that every disclosed handle component is always present. Rather, the term is used broadly, referring to the collection of components, but not specifically referring to or requiring the inclusion of any particular component. Likewise, other broad groupings of components disclosed herein, such as the syringe 110 or syringe body 112 and the plunger 120, may also refer to collections of individual subcomponents. Use of these terms should also be considered non-limiting, as each sub-component may or may not be present in every embodiment.

As shown in FIG. 1, a fluid reservoir 116 may be defined by the space enclosed by the inside walls of the syringe body 112 between the plunger seal 122 and the distal end 114 of the syringe body 112. Accordingly, movement of the plunger seal 122 with respect to the syringe body 112 will alter the size and volume of the fluid reservoir 116.

Figure 2:
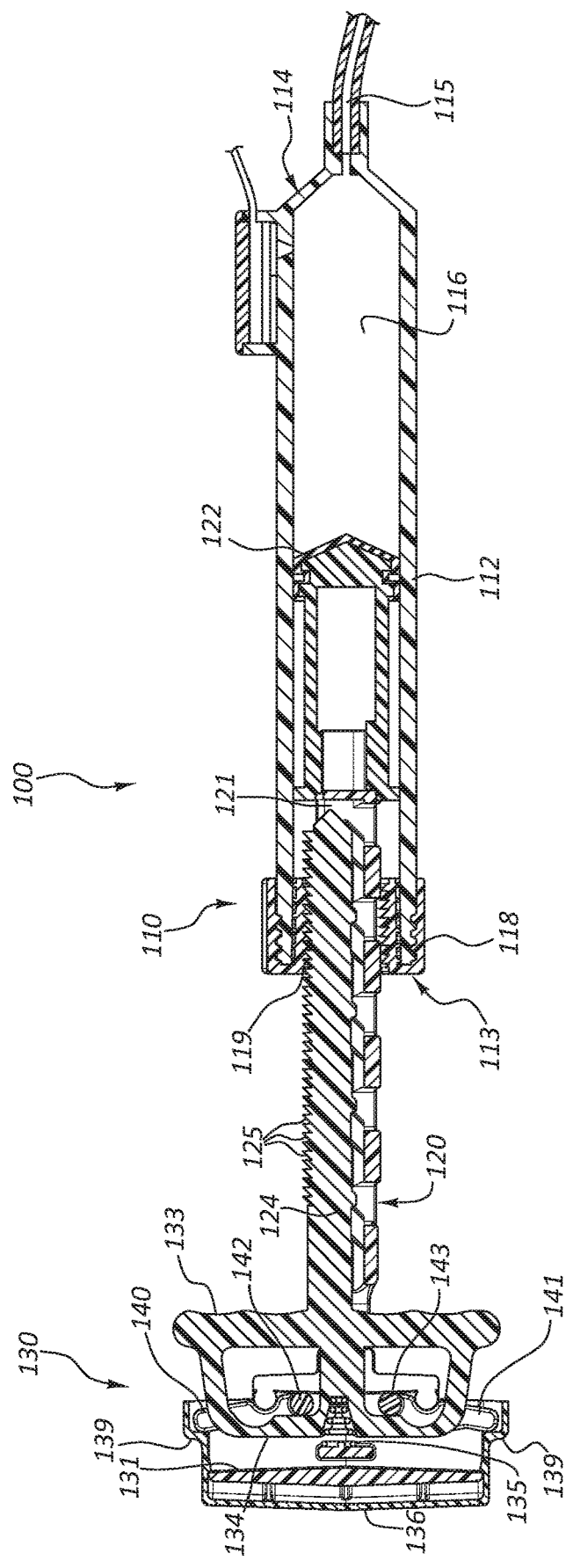
FIG. 2 is a cross sectional view of the inflation device of FIG. 1 taken through plane 2-2.

As shown in FIGS. 1 and 2, in some embodiments, the syringe 110 may include a nut 118, coupled to the proximal end 113 of the syringe body 112. The nut 118 may utilize threads or other coupling mechanisms to couple the nut 118 to the syringe body 112. The nut 118 may additionally include internal nut threads 119 configured to couple the nut 118 to a portion of the plunger 120. The plunger 120 may also include external plunger threads 125 configured to couple the plunger 120 to the nut 118. The plunger 120 may thus be translated longitudinally with respect to the syringe body 112 by rotating the plunger 120 such that the interaction of the nut threads 119 and the plunger threads 125 results in the longitudinal translation of the plunger 120.

Thus, when the plunger threads 125 and the nut threads 119 are engaged, movement of the plunger 120 is constrained with respect to the syringe body 112, though the plunger 120 is not necessarily fixed with respect to the syringe body 112. For example, the plunger 120 may be rotatable, but not directly translatable, when the threads 125, 119 are engaged.

Figure 3:
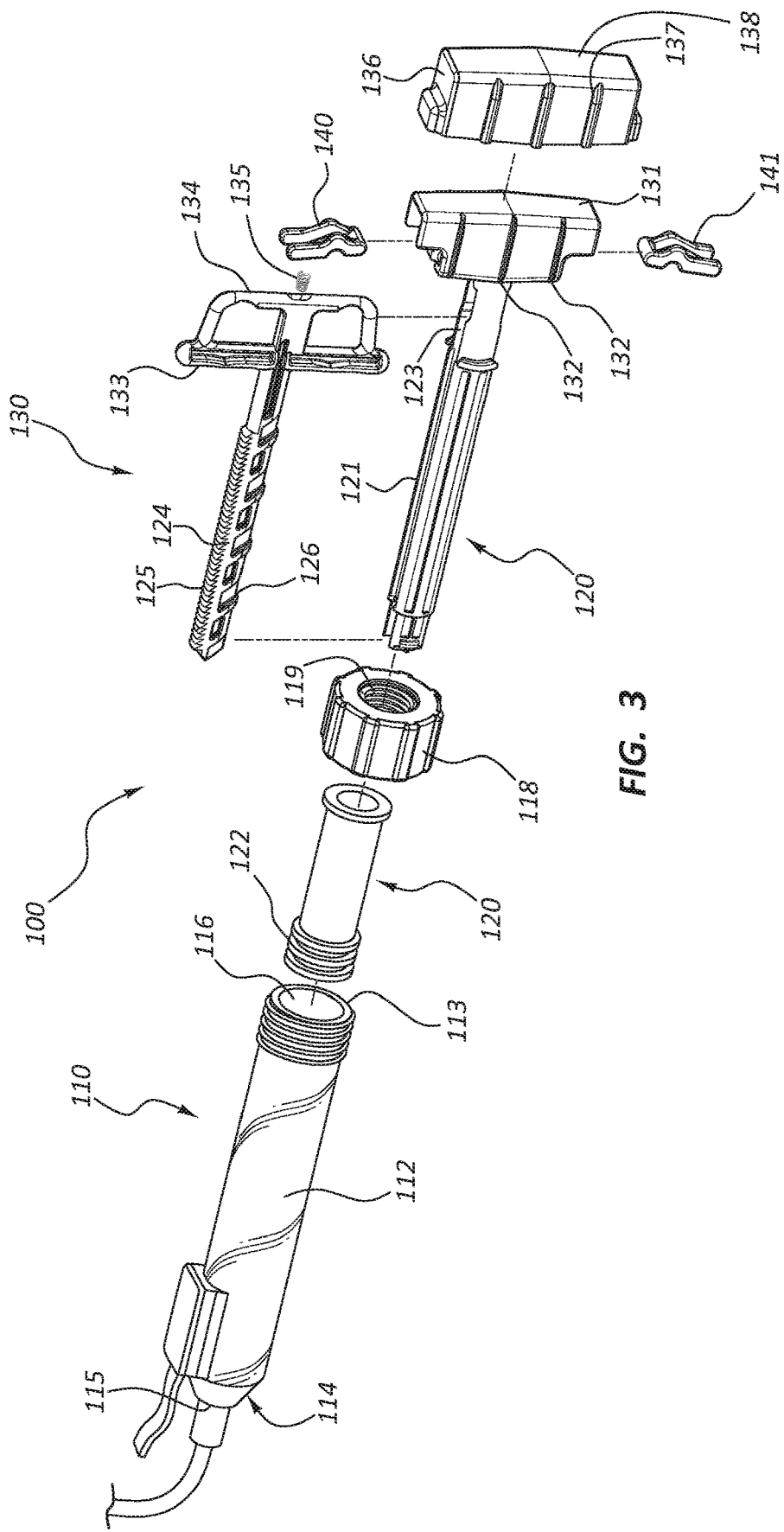
FIG. 3 is an exploded view of the inflation device of FIG. 1.
Figure 4:
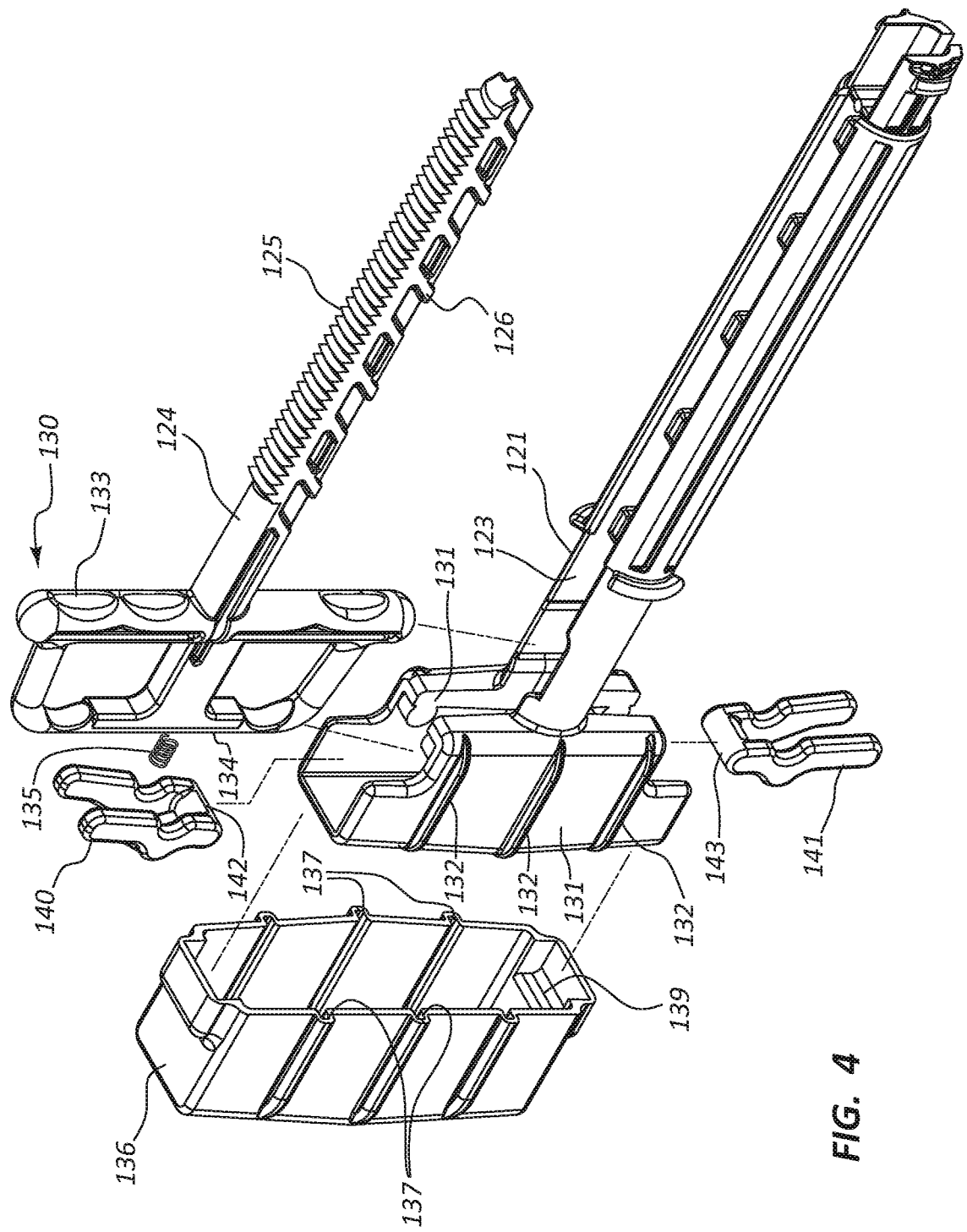
FIG. 4 is an exploded view of a portion of the handle of the inflation device of FIG. 1.
Figure 5:
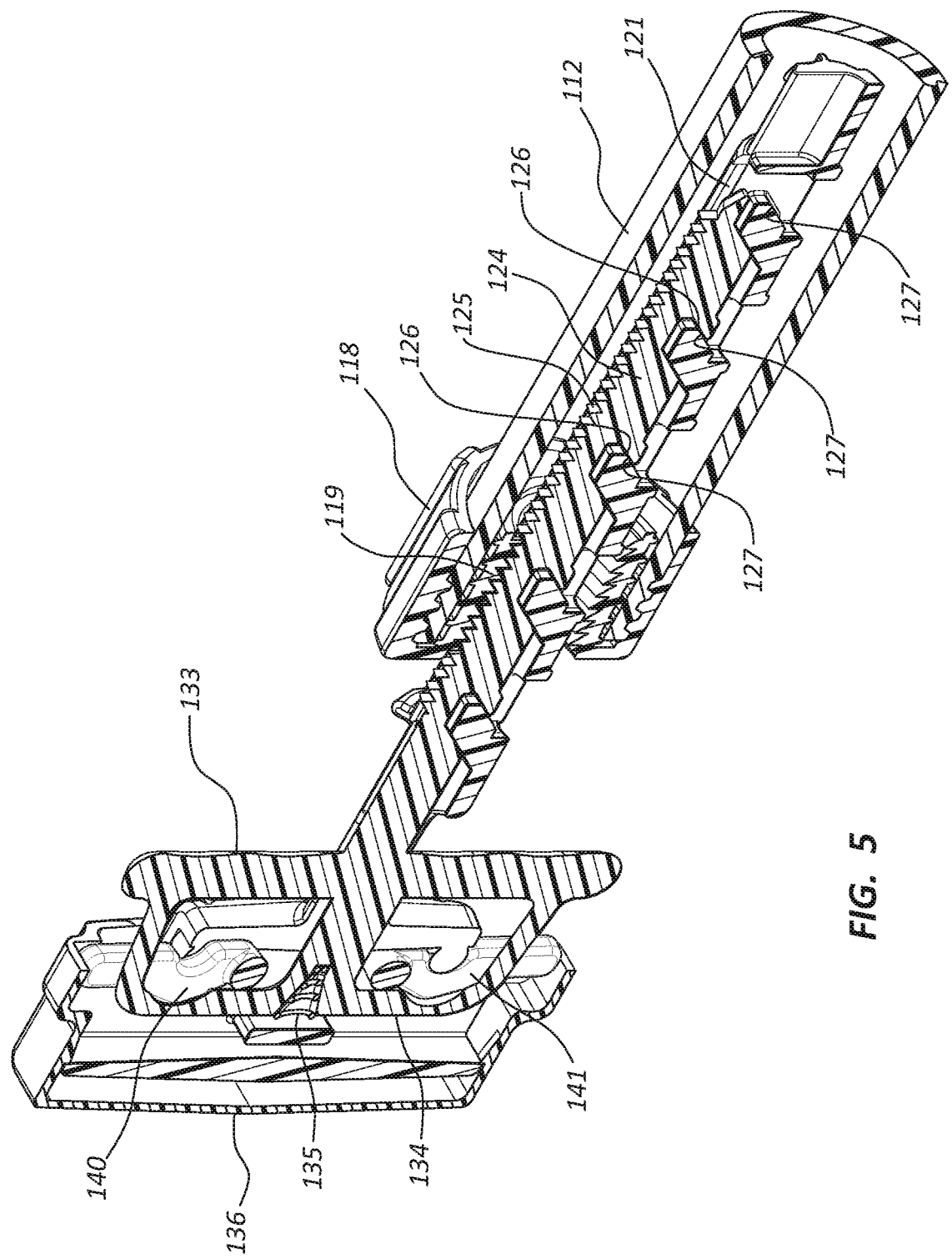
FIG. 5 is a cross sectional view of a portion of the inflation device of FIG. 1.

The plunger threads 125 may be configured such that they may be retracted within the plunger shaft 121. As shown in FIGS. 3 and 4, in some embodiments, the plunger threads 125 do not extend 360 degrees around the axis of the plunger shaft 121. Furthermore, as shown in FIGS. 1-4, the plunger threads 125 may be formed on a thread rail 124 which may be disposed within a groove 123 in the plunger shaft 121.

The thread rail 124 may be configured such that interaction between angled surfaces 126 on the thread rail 124 and the angled surfaces 127 (FIG. 5) within the groove 123 interact such that the plunger threads 125 may be retractable within the plunger shaft 121. The relationship between the angled surfaces 126 on the thread rail 124 and the angled surfaces 127 within the groove 123 (FIG. 4) shown in FIGS. 5, 8A, and 8B. Translation of the thread rail 124 in the proximal direction simultaneously causes the thread rail 124 to retract toward the center axis of the plunger shaft 121 due to the interaction of the angled surfaces 126 on the thread rail 124 with the angled surfaces 127 in the groove 123. Similarly, translation of the thread rail 124 in the distal direction causes the thread rail 124 to move away from the center axis of the plunger shaft 121. In the illustrated embodiment, a distally oriented biasing force acting on the thread rail 124 may bias the plunger threads 125 to the non-retracted position. It will be appreciated by one of ordinary skill in the art having the benefit of this disclosure that it is within the scope of this disclosure to modify the angles and interfaces such that a distally oriented biasing force on the thread rail 124 would bias the plunger threads 125 in the retracted position. As mentioned above, analogous mechanisms are disclosed in U.S. Pat. Nos. 5,047,015; 5,057,078; 5,163,904; and 5,209,732.

FIGS. 8A and 8B illustrate two possible positions of the thread rail 124 with respect to the internal nut threads 119 and the plunger shaft 121. FIG. 8A shows thread rail 124 disposed in a non-retracted position, such that the plunger threads 125 are engaged with the internal nut threads 119. FIG. 8B shows the thread rail 124 sufficiently retracted into the plunger shaft 121 that the plunger threads 125 are not engaged with the internal nut threads 119.

Embodiments which utilize retractable threads may allow a user to displace the plunger shaft 121 relative to the syringe body 112 either through rotation of the plunger shaft 121 (and the subsequent interaction of threads), or by retracting the plunger threads 125 and displacing the plunger shaft 121 by applying opposing forces on the plunger shaft 121 and the syringe body 112. (The forces, of course, may move the plunger shaft 121 distally or proximally with respect to the syringe body 112). Both methods of displacement may be utilized during the course of a single therapy.

FIG. 6 is a cross sectional view of the inflation device of FIG. 1 with fluid 50 disposed within the reservoir 116. In some instances, a practitioner may desire to quickly displace the plunger shaft 121, for instance, while priming the inflation device or while priming or deflating an attached medical device such as a balloon. Quick displacement of the plunger shaft 121 may be accomplished by retracting the plunger threads 125 and sliding the plunger shaft 121 relative to the syringe body 112. For example, a practitioner may quickly fill the reservoir 116 with fluid 50 by disengaging the plunger threads 125 and pulling the plunger shaft 121 in a proximal direction with respect to the syringe body 112. Further, a practitioner may quickly force fluid 50 into lines leading to other device or quickly expel unwanted air bubbles from the reservoir 116 by retracting the plunger threads and repositioning the plunger shaft 121.

In other instances, the practitioner may desire more precise control over the position of the plunger shaft 121 (for example when displacing the plunger shaft 121 in order to adjust the fluid pressure within the reservoir 116) or it may simply be difficult or impossible without a mechanical advantage to displace the plunger shaft 121 due to high fluid pressure within the reservoir 116. In these instances, the practitioner may opt to displace the plunger shaft 121 by rotation of the plunger shaft 121.

Referring back to FIG. 4, the handle 130 of the inflation device 100 (FIG. 1) may include components which enable a practitioner to retract the thread rail 124 of the plunger 120. In some embodiments, the plunger shaft 121 may be fixed to a first member such as inner member 131 of the handle 130. The thread rail 124 may be fixed to a trigger 133 component of the handle. Further, a biasing component 135 may be configured to bias the trigger 133 in a distal direction. Because the trigger 133 is fixed to the thread rail 124, a distally oriented force on the trigger 133 will result in a distally oriented force on the thread rail 124 as well. The force provided by the biasing component 135 (hereafter referred to as the biasing force) may thus bias the thread rail 124 in a non-retracted position as described above. Conversely, overcoming the biasing force and translating the trigger 133 in a proximal direction with respect to the plunger shaft 121 and inner member 131, may retract the plunger threads 125.

In some embodiments the handle 130 may further include a second member such as outer sleeve 136 and one or more levers 140, 141. The levers 140, 141 may be disposed such that they provide mechanical advantage, enabling the user to more easily overcome the biasing force and draw the trigger 133 toward the inner member 131.

Referring particularly to FIGS. 4, 6, 7A, and 7B, portions of the handle 130 which interact with lever 140 may be the mirror image of the portions of the handle which interact with lever 141. Thus, in some embodiments, disclosure provided in connection with one lever is equally applicable to the other lever. Furthermore, it is within the scope of this disclosure to include levers on each side of the handle which are not identical or to include a single lever.

As is particularly shown in FIGS. 7A and 7B, the outer sleeve 136 contacts lever 140 at point A. The outer sleeve 136 may include a shoulder 139 configured to contact lever 140. A distally oriented force applied to the outer sleeve 136 will thus exert a distally oriented force on lever 140 at point A through contact of the shoulder 139 with lever 140. Furthermore, lever 140 may be configured to pivot about pivot point B, and the cross bar 142 (FIG. 6) of lever 140, may thus exert a proximally oriented force on a top member 134 of the trigger 133 at point C. Thus, a force which acts distally on the outer sleeve 136 is transferred by the levers 140, 141 and results in a proximal force on the trigger 133. As discussed above, in the illustrated embodiment, a proximal force on the trigger 133 causes the thread rail 124 to retract.

It is within the scope of this disclosure to alter the shape or form of the levers 140, 141. For instance lever 140 is shown with a inside radius near the pivot point B which mates with an outside radius formed on a portion of the inner member 131. It is within the scope of this disclosure to alter the design such that the outside radius is formed on the lever and the inside radius on the inner member 131. Similar design modifications to the levers or any other component are equally within the scope of this disclosure.

It will be appreciated by one of ordinary skill in the art having the benefit of this disclosure that, in many instances, a proximal force will be applied to the trigger 133 at the same time a distal force is applied to the outer sleeve 136. For example, when the handle 130 is grasped by a user, the user may actuate the handle 130 by squeezing the trigger 133 with his or her fingers. This action may coincide with a distally oriented force exerted on the outer sleeve 136 by the palm of the user's hand. Examples of such forces are illustrated in FIG. 7B, where force X may be due to contact with the palm of the user's hand while the two forces designated Y may be in response to contact with the fingers of the user. Accordingly, the forces applied in this manner may be understood as a proximal force on the trigger 133 and a distal force on the outer sleeve 136. The mechanism of the levers 140, 141 essentially combines these forces into a single force acting to retract the thread rail 124.

The relative distance between each contact point on the lever 140 (A and C) and the pivot point (B) may create mechanical advantage, allowing a user to more easily overcome the biasing force and retract the plunger threads 125. As the distance between A and B increases relative to the distance between C and B, a distal input force at point A will result in a greater resultant force at point C. This mechanism also requires the input point A to travel a larger distance than the output displacement of point C. A mechanism such as that described above may be used in connection with a trigger activated retraction mechanism for an inflation device as described above, or any other device which similarly uses a squeeze-type handle as an input to control a mechanism.

In the illustrated embodiment, the distance between point A and point B is greater than the distance between point B and point C, thus an input force on the outer sleeve 136 creates a larger resultant force on the trigger 133. In other embodiments, the design could be modified such that the distance from point B to point C is greater than the distance from point A to point B. Moreover, the levers 140, 141 may be modified such that the pivot point (B) is located at one end of each lever, rather than the pivot point located between the force transferring contact points (A, C) as in the illustrated embodiment. Furthermore, any combination of these alternate designs is within the scope of this disclosure, including designs where each of two levers has a different design, the handle includes a single lever, or compliant mechanisms are utilized to perform transfer force and provide mechanical advantage.

A handle configured to provide a mechanical advantage when retracting a thread rail may be desirable for certain therapies which require large syringes or high pressure. Such therapies may also require a larger biasing force due to the size of the device or the pressure within the device. A handle providing a mechanical advantage may make devices configured for such therapies easier to use.

As described above, and illustrated in the figures, in some embodiments, the levers 140, 141 may not be pinned or otherwise mechanically coupled to any of the other parts. In some embodiments, the levers 140, 141 may be only be constrained due to contact with other components of the device. Likewise, the outer sleeve 136 may not be mechanically fastened to any other component, though—like the levers 140, 141—contact between portions of the outer sleeve 136 and other components may be utilized to secure the position of the outer sleeve 136 with respect to the other components. Thus, in some embodiments the levers 140, 141 and outer sleeve 136 may be allowed "float" with respect to the other parts. A floating assembly as described above may allow certain components multiple degrees of freedom with respect to the other parts. For example, as explained below, in some embodiments the trigger 133 may be displaced in both the longitudinal and transverse directions (with respect to the outer sleeve 136) when the trigger 133 is actuated.

As shown in FIGS. 3 and 4, the outer sleeve 136 may also include slots 137 configured to mate with ridges 132 formed on the outer surface of the inner member 131. The interaction between these slots 137 and ridges 132 constrains the movement of the outer sleeve 136 with respect to the inner member 131; that is, the two components may only travel (with respect to each other) in a single direction, parallel to the longitudinal axis of the syringe body 112. As mentioned above, in the illustrated embodiment, the trigger 133 travels in a direction transverse to the longitudinal axis of the syringe body 112 (in addition to travel along the longitudinal axis) when it is compressed, due to the interaction of the angled surfaces 126, 127 of the thread rail 124 and the plunger shaft 121. Ridges and slots, such as those of the illustrated embodiment (132, 137), may provide a degree of usability and comfort to the device, as the portion of the outer sleeve 136—which may be in contact with the palm of the user in some instances—does not slide in a transverse direction.

Many design modifications relating to the outer sleeve 136 are within the scope of the current disclosure. For example, in the illustrated embodiments, the outer sleeve 136 has a cap-like shape, fitting over the inner member 131. In other embodiments, the outer sleeve 136 may instead be designed as a button which slides into the inner member 131 when it is compressed. Likewise, any other longitudinally actuatable component may be utilized in place of the outer sleeve 136.

The handle mechanism described above, and shown in each of FIG. 2-8, may also be utilized to change the location and direction of an input force required to retract the plunger threads 125. Essentially, the mechanism allows a user to draw the trigger 133 toward the inner member 131 (and thus retract the threads) solely by applying a distally oriented force to the top surface 138 of the outer sleeve 136. As outlined above, the levers 140, 141 transfer this force to the trigger 133 which retracts the plunger threads 125.

In some instances a user, such as a medical practitioner, may desire to displace the plunger 120 in a distal direction with only one hand. This may be accomplished by grasping the syringe body 112 and using a surface, for example a table top, to apply a distally oriented force on the top surface 138 of the outer sleeve 136. In this manner, a mechanism such as that described above may enable a practitioner to displace the plunger in a one-handed fashion.

Figure 9:
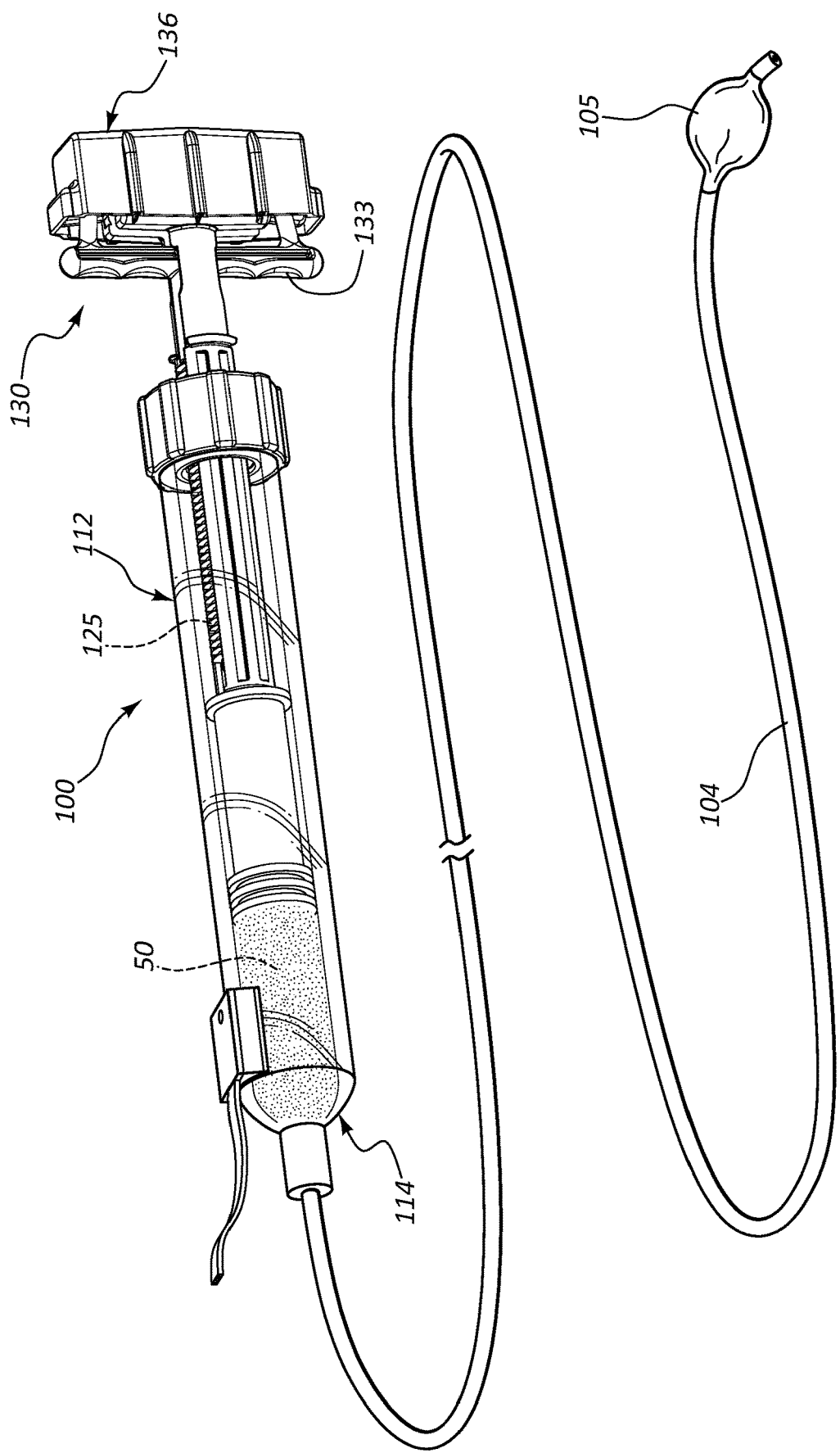
FIG. 9 is a perspective view of the inflation device of FIG. 1 with fluid disposed within the device and a balloon coupled to the inflation device.

FIG. 9 is a perspective view of the inflation device 100 of FIG. 1 with fluid 50 disposed within the device and a balloon 105 coupled to the inflation device 100 via a delivery line 104. Referring now to components shown in FIG. 9 as well as the other figures, in some instances it may be desirable to operate the syringe 110 "one-handed" as described above in order to prime the system. For example, a practitioner may utilize the inflation device 100 in connection with a therapy which includes the balloon 105, such as an angioplasty. The practitioner may initially fill the syringe body 112 with fluid 50, such as a contrast fluid, by drawing the plunger 120 back in the proximal direction. In some instances, the practitioner will do so by grasping the handle 130 of the inflation device with a first hand, while grasping the syringe body 112 with a second hand. The practitioner may then retract the plunger threads 125 by squeezing the trigger 133 and the outer sleeve 136 together with his or her first hand, then drawing the plunger 120 back in the proximal direction.

After a desired amount of fluid is disposed within the syringe body 112, the practitioner may orient the syringe such that the distal end 114 of the syringe body 112 is above the handle 130, so any air bubbles in the fluid will tend to rise to the distal end 114 of the syringe body 112. The practitioner may also shake, tap, or otherwise disturb the syringe 110 in order to facilitate movement of any air bubbles in the fluid. The practitioner may then prime the syringe 110 by displacing the plunger 120 in a distal direction with respect to the syringe body 112, thereby forcing the air bubbles from the syringe body 112.

In some instances the practitioner will displace the plunger 120 as described after first retracting the plunger threads 125. This may be accomplished in any manner disclosed herein, including the one handed operation described above. That is, the practitioner may prime the inflation device simply by grasping the syringe body 112 with one hand and using a fixed object or surface, such as a table top, to exert a distally directed force on the top surface 138 of the outer sleeve 136. The force on the outer sleeve 136 will both (1) retract the plunger threads 125 via the handle 130 mechanism and (2) act to displace the plunger 120 in a distal direction with respect to the syringe body 112. This orientation positions the syringe body 112 in a potentially desirable position to allow air to travel to the distal end 114 of the syringe body 112 while simultaneously orienting the handle 130 such that the top surface 138 of the outer sleeve 136 directly faces a horizontal surface such as a table. Thus, in some instances a physician may desire to prime the syringe 110 in this way due to the orientation of the syringe 110 as well as the ability to do so with one hand.

There may be other instances during therapy in which the practitioner desires to displace the plunger 120 distally using only one hand. In addition to priming the inflation device as described above, this method of advancing the plunger may also be employed to prime a device connected to the syringe 110, such as a balloon 105.

Without further elaboration, it is believed that one skilled in the art can use the preceding description to utilize the present disclosure to its fullest extent. The examples and embodiments disclosed herein are to be construed as merely illustrative and exemplary, and not a limitation of the scope of the present disclosure in any way. It will be apparent to those having skill in the art that changes may be made to the details of the above-described embodiments without departing from the underlying principles of the disclosure herein. It is intended that the scope of the invention be defined by the claims appended hereto and their equivalents.

The invention claimed is:

1. An apparatus for displacing fluid through a medical lumen, the apparatus comprising:
   a body;
   a plunger slidably coupled to the body and in selectable engagement with the body such that, when engaged, longitudinal displacement of the plunger relative to the body is constrained; and
   a handle operably coupled to the plunger, the handle comprising a first member configured such that distal displacement of the first member of the handle with respect to the plunger by a user disengages the plunger from the body, wherein the distal displacement of the first member of the handle causes a second member of the handle to be displaced proximally to disengage the second member from the body.

2. The apparatus of claim 1, wherein proximal displacement of the second member of the handle with respect to the plunger disengages the plunger from the body.

3. The apparatus of claim 2, wherein displacement of the first member of the handle and the second member of the handle toward each other disengages the plunger from the body.

4. The apparatus of claim 2, further comprising a lever disposed between the first member of the handle and the second member of the handle.

5. The apparatus of claim 4, wherein the lever provides a factor of mechanical advantage in disengaging the plunger from the body.

6. The apparatus of claim 1, wherein the second member comprises a plurality of threads in selectable engagement with the body, and wherein the distal displacement of the first member of the handle displaces the plurality of threads radially inward toward a longitudinal axis of the apparatus, such that the plurality of threads disengage from the body.

7. The apparatus of claim 1, wherein the first member is proximal to the second member.

8. A system for displacing fluid through a medical lumen, the system comprising:
a fluid reservoir;
a plunger longitudinally displaceable within the fluid reservoir such that displacement of the plunger in a first direction with respect to the fluid reservoir displaces fluid within the reservoir along the medical lumen;
a coupler constraining displacement of the plunger within the fluid reservoir; and
an actuator operably coupled to the plunger to selectively engage and disengage the plunger with the coupler such that solely applying a force in the first direction to a first member of the actuator by a user in the first direction disengages the plunger from the coupler.

9. The apparatus of claim 8, wherein displacement of a second member of the actuator in the second direction disengages the coupler.

10. The apparatus of claim 9, further comprising a lever disposed between the first member of the actuator and the second member of the actuator.

11. The apparatus of claim 10, wherein the lever provides a factor of mechanical advantage in disengaging the coupler.

12. The apparatus of claim 10, wherein the lever transfers a force applied to the first member of the actuator to the second member of the actuator.

13. The apparatus of claim 9, wherein the first member is proximal to the second member.

14. The apparatus of claim 8, wherein the plunger comprises a plurality of threads displaceable radially inward to disengage the coupler.

15. An apparatus for displacing fluid through a medical lumen, the apparatus comprising:
a body;
a plunger slidably coupled to the body and in selectable engagement with the body such that, when engaged, longitudinal displacement of the plunger relative to the body is constrained; and
a handle operably coupled to the plunger, wherein
distal displacement of a first member of the handle with respect to the plunger by a distally oriented force applied to the first member by a user disengages the plunger from the body, and
proximal displacement of a second member of the handle with respect to the plunger by the first member of the handle disengages the second member from the body.

16. A method of displacing fluid through a medical lumen, the method comprising:
displacing a first member of an actuator in a distal direction relative to a plunger by a distally oriented force applied to the first member by a user to disengage the plunger from a fluid reservoir; and
displacing fluid from the fluid reservoir into the medical lumen by displacing the plunger in the distal direction.

17. The method of claim 16, wherein the step of displacing the first member of the actuator in the distal direction causes displacement of a second member of the actuator in a proximal direction to disengage the plunger from the fluid reservoir.

18. The method of claim 16, wherein the step of displacing the first member of the actuator in the distal direction comprises displacing a plurality of threads coupled to the plunger in a radially inward direction in response to the distal displacement of the first member.

19. The method of claim 16, wherein the step of displacing the first member of the actuator in the distal direction comprises:
gripping a member of the fluid reservoir with only one hand of the user;
contacting the first member of the actuator against an environmental object such that the environmental object applies the distally oriented force to the first member.

20. The method of claim 16, further comprising displacing a lever operably coupled to the actuator.

* * * * *